United States Patent [19]

Oka et al.

[11] 4,288,590

[45] * Sep. 8, 1981

[54] 7-[Dα-(4-HYDROXY-1,5-NAPHTHYRIDINE-3-CARBOXAMIDO)-α-ARYLACETAMIDO]-3-(N,N-DIMETHYL-AMINOMETHYL-PYRIDINIUM) METHYL-3-CEPHEM-4-CARBOXYLATES

[75] Inventors: Masahisa Oka; Jun Okumura, both of Yokohama; Takayuki Naito, Kawasaki, all of Japan

[73] Assignee: Bristol-Myers Company, New York, N.Y.

[*] Notice: The portion of the term of this patent subsequent to Apr. 15, 1997, has been disclaimed.

[21] Appl. No.: 121,623

[22] Filed: Feb. 14, 1980

[51] Int. Cl.$^3$ .............................. C07D 501/40
[52] U.S. Cl. ...................... 544/25; 424/246
[58] Field of Search ..................... 544/25; 424/246

[56] References Cited

U.S. PATENT DOCUMENTS

| 3,217,000 | 11/1965 | Flynn | 260/243 |
|---|---|---|---|
| 3,225,038 | 12/1978 | Flynn | 260/243 |
| 3,261,832 | 2/1966 | Cowley et al. | 260/243 |
| 3,270,012 | 8/1966 | Higgins | 260/243 |
| 3,280,118 | 10/1966 | Fardley et al. | 260/243 |
| 3,303,193 | 2/1967 | Godfrey | 260/243 |
| 3,449,338 | 6/1969 | Flynn | 260/243 |
| 3,479,350 | 11/1969 | Fardley et al. | 260/243 |
| 3,560,489 | 2/1971 | Morin | 260/243 |
| 3,945,995 | 3/1976 | Yamada et al. | 260/239.1 |
| 4,061,748 | 12/1977 | Yamada et al. | 424/246 |
| 4,065,619 | 12/1977 | Morimoto et al. | 544/25 |
| 4,117,126 | 9/1978 | Yamada et al. | 424/246 |
| 4,138,554 | 2/1979 | Naito et al. | 544/22 |
| 4,156,724 | 5/1979 | Yamada et al. | 424/246 |
| 4,160,087 | 7/1979 | Yamada et al. | 544/28 |
| 4,165,373 | 8/1979 | Yamada et al. | 424/246 |
| 4,198,504 | 4/1980 | Naito et al. | 544/25 |

*Primary Examiner*—Nicholas S. Rizzo
*Attorney, Agent, or Firm*—Herbert W. Taylor, Jr.

[57] ABSTRACT

7-[D-α-(4-Hydroxy-1,5-naphthyridine-3-carboxamido)-α-phenyl (and thienyl and substituted phenyl) acetamido]-3-(2-, 3- or 4-N,N-dimethylaminomethyl-pyridinium)methyl-3-cephem-4-carboxylates were synthesized and found to have potent antibacterial activity in vitro especially against many strains of *Pseudomonas aeruginosa*.

26 Claims, No Drawings

7-[Dα-(4-HYDROXY-1,5-NAPHTHYRIDINE-3-CARBOXAMIDO)-α-ARYLACETAMIDO]-3-(N,N-DIMETHYL-AMINOMETHYLPYRIDINIUM) METHYL-3-CEPHEM-4-CARBOXYLATES

BACKGROUND OF THE INVENTION

1. Field of the Invention

The chemicals of the present invention belong to the class of antibacterial agents commonly called cephalosphorins.

2. Description of the Prior Art

Early U.S. patents in which there is a carbamoyl substituent on the 3-N-pyridylmethyl group (also called 3-pyridiniummethyl) include 3,217,000, 3,225,038, 3,261,832, 3,270,012, 3,280,118, 3,449,338 and 3,479,350 and very recently see 4,065,619.

7-(D-α-aminophenylacetamido)cephalosporanic acid was described, for example, in U.S. Pat. No. 3,303,193 and 3,560,489; the latter includes the 3-(4'-carbamoyl-pyridinomethyl) derivative.

Sodium 7-[D-α-(4-hydroxy-1,5-naphthyridine-3-carboxamido)-α-phenyl- or substituted-phenyl-acetamido]-3-acetoxy(or 3-substituted thio)-methyl-3-cephem-4-carboxylates are described in U.S. Pat. Nos. 4,061,748, 4,117,126, 4,156,724, 4,160,087 and 4,165,373. See also U.S. Pat. No. 4,138,554.

For compounds similar to those of the present invention except that the substituents on the pyridine ring are acidic rather than basic see U.S. patent application Ser. No. 957,113 filed Nov. 2, 1978, now U.S. Pat. No. 4,198,504.

U.S. Pat. No. 3,945,995 describes the preparation of the N-hydroxysuccinimido ester of 4-hydroxy-1,5-naphthyridine-3-carboxylic acid.

SUMMARY OF THE INVENTION

There is provided by the present invention the compounds having the D-configuration in the 7-sidechain and the formula

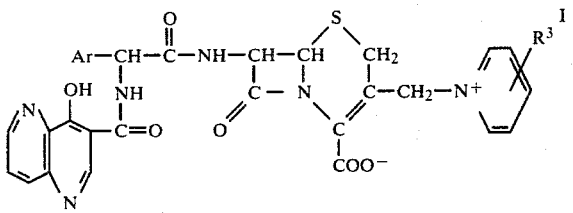

wherein Ar is

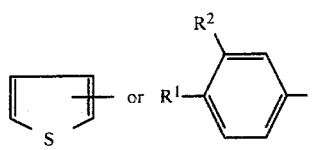

and $R^1$ is hydrogen or hydroxy and $R^2$ is hydrogen, hydroxy, methyl, methoxy or chloro and $R^3$ is N,N-dimethylaminomethyl.

The preferred compounds of the present invention are those of formula I in which $R^1$ and $R^2$ are hydrogen or $R^1$ is hydroxy and $R^2$ is hydrogen, chloro or hydroxy.

The following are the preferred species of the present invention:

7-[D-α-(4-Hydroxy-1,5-naphthyridine-3-carboxamido)-α-phenylacetamido]-3-(3-N,N-dimethylaminomethylpyridinium)methyl-3-cephem-4-carboxylate;

7-[D-α-(4-Hydroxy-1,5-naphthyridine-3-carboxamido)-α-phenylacetamido]-3-(4-N,N-dimethylaminomethylpyridinium)methyl-3-cephem-4-carboxylate;

7-[D-α-(4-Hydroxy-1,5-naphthyridine-3-carboxamido)-α-(4-hydroxyphenyl)acetamido]-3-(3-N,N-dimethylaminomethylpyridinium)methyl-3-cephem-4-carboxylate;

7-[D-α-(4-Hydroxy-1,5-naphthyridine-3-carboxamido)-α-(4-hydroxyphenyl)acetamido]-3-(4-N,N-dimethylaminomethylpyridinium)methyl-3-cephem-4-carboxylate;

7-[D-α-(4-Hydroxy-1,5-naphthyridine-3-carboxamido)-α-(3,4-dihydroxyphenyl)acetamido]-3-(3-N,N-dimethylaminomethylpyridinium)methyl-3-cephem-4-carboxylate;

7-[D-α-(4-Hydroxy-1,5-naphthyridine-3-carboxamido)-α-(3,4-dihydroxyphenyl)acetamido]-3-(4-N,N-dimethylaminomethylpyridinium)methyl-3-cephem-4-carboxylate;

7-[D-α-(4-Hydroxy-1,5-naphthyridine-3-carboxamido)-α-(3-chloro-4-hydroxyphenyl)acetamido]-3-(3-N,N-dimethylaminomethylpyridinium)methyl-3-cephem-4-carboxylate;

7-[D-α-(4-Hydroxy-1,5-naphthyridine-3-carboxamido)-α-(3-chloro-4-hydroxyphenyl)acetamido]-3-(4-N,N-dimethylaminomethylpyridinium)methyl-3-cephem-4-carboxylate;

7-[D-α-(4-Hydroxy-1,5-naphthyridine-3-carboxamido)-α-(3-methyl-4-hydroxyphenyl)acetamido]-3-(3-N,N-dimethylaminomethylpyridinium)methyl-3-cephem-4-carboxylate;

7-[D-α-(4-Hydroxy-1,5-naphthyridine-3-carboxamido)-α-(3-methyl-4-hydroxyphenyl)acetamido]-3-(4-N,N-dimethylaminomethylpyridinium)methyl-3-cephem-4-carboxylate;

7-[D-α-(4-Hydroxy-1,5-naphthyridine-3-carboxamido)-α-(3-methoxy-4-hydroxyphenyl)acetamido]-3-(3-N,N-dimethylaminomethylpyridinium)methyl-3-cephem-4-carboxylate;

7-[D-α-(4-Hydroxy-1,5-naphthyridine-3-carboxamido)-α-(3-methoxy-4-hydroxyphenyl)acetamido]-3-(4-N,N-dimethylaminomethylpyridinium)methyl-3-cephem-4-carboxylate;

7-[D-α-(4-Hydroxy-1,5-naphthyridine-3-carboxamido)-α-(3-thienyl)acetamido]-3-(3-N,N-dimethylaminomethylpyridinium)methyl-3-cephem-4-carboxylate; and 7-[D-α-(4-Hydroxy-1,5-naphthyridine-3-carboxamido)-α-(3-thienyl)acetamido]-3-(4-N,N-dimethylaminomethylpyridinium)methyl-3-cephem-4-carboxylate.

Of all of these we presently prefer BB-S651 which is 7-[D-α-(4-hydroxy-1,5-naphthyridine-3-carboxamido)-α-(4-hydroxyphenyl)acetamido]-3-(3-N,N-dimethylaminomethylpyridinium)methyl-3-cephem-4-carboxylate hydrochloride.

As illustrated in terms of the preferred species, the compounds of the present invention are shown in the zwitterion form thus

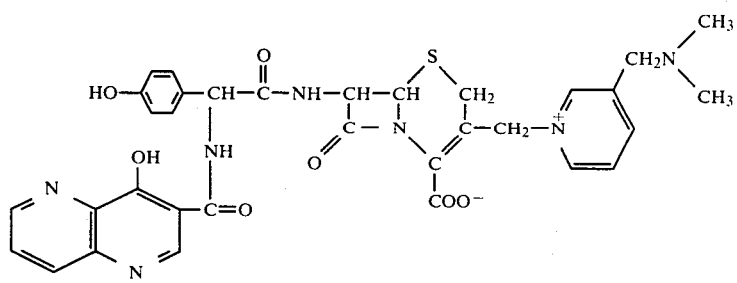

It is to be observed that this molecule still contains a basic nitrogen which, under sufficiently acid conditions, can form a nontoxic, therapeutically acceptable acid addition salt which also is part of the present invention and is the equivalent of the zwitterion form. Such salts include mineral acid addition salts such as the hydrochloride, hydrobromide, hydriodide, sulfate, sulfamate and phosphate and organic acid addition salts such as the maleate, acetate, citrate, oxalate, succinate, benzoate, tartrate, fumarate, malate, mandelate, ascorbate and the like.

There is also provided by the present invention the process for the preparation of a compound having the formula

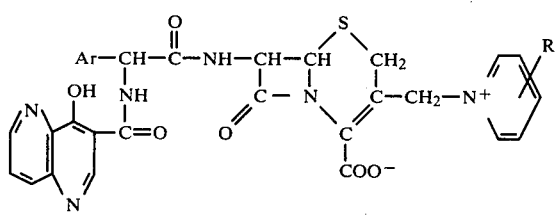

wherein Ar is

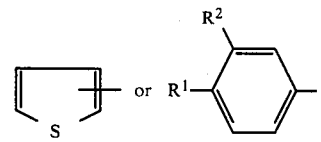

wherein $R^1$ is hydrogen or hydroxy and $R^2$ is hydrogen, hydroxy, methyl, methoxy or chloro and $R^3$ is N,N-dimethylaminomethyl by reacting 2-, 3- or 4-N,N-dimethylaminomethylpyridine with a compound having the formula

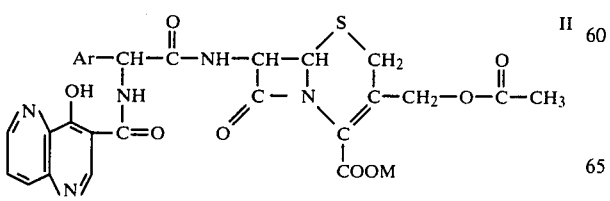

wherein Ar is

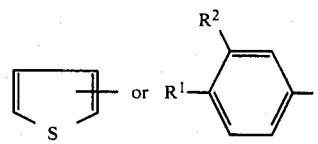

wherein $R^1$ is hydrogen or hydroxy and $R^2$ is hydrogen, hydroxy, methyl, methoxy or chloro and M is hydrogen or a metal and preferably an alkali metal such as sodium or potassium. This reaction is preferably carried out in a solvent and water is preferred. The reaction is carried out at a temperature from room temperature to 100° C.; it is expedited by heating as to about 50° C. Roughly equimolar amounts are used with the preferred procedure being the use of an excess of the substituted pyridine, that is, ten to forty percent. It is also preferred to have KSCN present in the reaction mixture and preferably in an amount by weight which is two to six times (and most preferably four times) the weight of the cephalosporanic acid or its salt.

There is also provided, according to the present invention, another process for the preparation of a compound having the formula

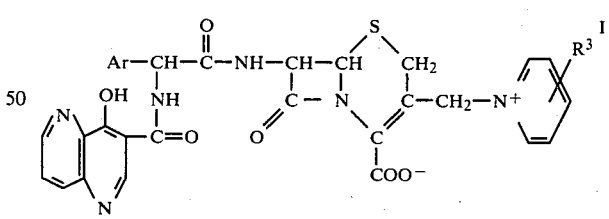

wherein Ar is

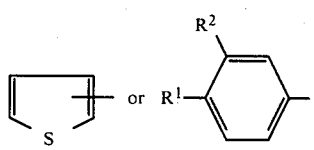

wherein $R^1$ is hydrogen or hydroxy or hydroxy and $R^2$ is hydrogen, hydroxy, methyl, methoxy or chloro and $R^3$ is N,N-dimethylaminomethyl which comprises reacting a compound of the formula

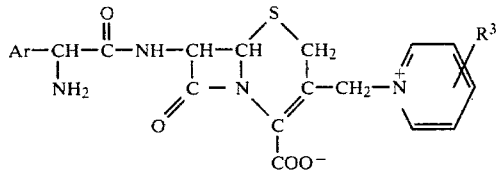

wherein Ar is

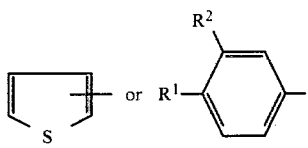

wherein $R^1$ is hydrogen or hydroxy and $R^2$ is hydrogen, hydroxy, methyl, methoxy or chloro and $R^3$ is N,N-dimethylaminomethyl with an acylating derivative of the acid having the formula

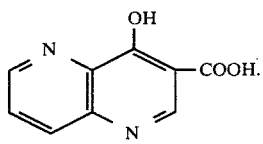

The compounds of the present invention are prepared in the second process by coupling, with the compound designated III, the acid IV or its functional equivalent as an acylating agent for a primary amino group.

Thus, with respect to said acid IV to be used to couple with compound III, functional equivalents include the corresponding acid anhydrides, including mixed anhydrides and particularly the mixed anhydrides prepared from stronger acids such as the lower aliphatic monoesters or carbonic acid, or alkyl and aryl sulfonic acids and of more hindered acids such as diphenylacetic acid. In addition, an acid azide or an active ester or thioester (e.g., with p-nitrophenol, 2,4-dinitrophenol, thiophenol, thioacetic acid) may be used or the free acid itself may be coupled with compound III after first reacting said free acid with N,N'-dimethylchloroformiminium chloride [(cf. Great Britain No. 1,008,170 and Novak and Weichet, Experientia XXI, 6, 360 (1965)] or by the use of enzymes or of an N,N'-carbonyldiimidazole or an N,N'-carbonylditriazole (cf. South African patent specification 63/2684) or a carbodiimide reagent [especially N,N'-dicyclohexylcarbodiimide, N,N'-diisopropylcarbodimmide or N-cyclohexyl-N'-(2-morpholinoethyl)carbodiimide; cf. Sheehan and Hess, *J. Amer. Chem. Soc.*, 77, 1967 (1955)], or of alkylylamine reagent [cf. R. Buijle and H. G. Viehe, *Angew. Chem. International Edition* 3, 582, (1964)] or of an isoxazolium salt reagent [cf. R. B. Woodward, R. A. Olofson and H. Mayer, *J. Amer. Chem. Soc.*, 83, 1010 (1961)], or of a ketenimine reagent [cf. C. L. Stevens and M. E. Munk, *J. Amer. Chem. Soc.*, 80, 4065 (1958)] or of hexachlorocyclotriphosphatriazine or hexabromocyclotriphosphatriazine (U.S. Pat. No. 3,651,050) or of diphenylphosphoryl azide [DPPA; *J. Amer. Chem. Soc.*, 94, 6203–6205 (1972)] or of diethylphosphoryl cyanide [DEPC; *Tetrahedron Letters* No. 18, pp. 1595–1598 (1973)] or of diphenyl phosphite [*Tetrahedron Letters* No. 49, pp. 5047–5050 (1972)]. Another equivalent of the acid chloride is a corresponding azolide, i.e., an amide of the corresponding acid whose amide nitrogen is a member of a quasiaromatic five-membered ring containing at least two nitrogen atoms, i.e., imidazole, pyrazole, the triazoles, benzimidazole, benzotriazole and their substituted derivatives. As an example of the general method for the preparation of an azolide, N,N'-carbonyldiimidazole is reacted with a carboxylic acid in equimolar proportions at room temperature in tetrahydrofuran, chloroform, dimethylformamide or a similar inert solvent to form the carboxylic acid imidazolide in practically quantitative yield with liberation of carbon dioxide and one mole of imidazole. Dicarboxylic acids yield diimidazolide. The by-product, imidazole, precipitates and may be separated and the imidazolide isolated, but this is not essential. The methods for carrying out these reactions to produce a cephalosporin and the methods used to isolate the cephalosporin so produced are well known in the art.

Mention was made above of the use of enzymes to couple the free acid IV with compound III. Included in the scope of such processes are the use of an ester, e.g., the methyl ester, of that free acid with enzymes provided by various microorganisms, e.g. those described by T. Takahashi et al., *J. Amer. Chem. Soc.*, 94(11), 4035–4037 (1972) and by T. Nara et al., *J. Antibiotics* (Japan) 24(5), 321–323 (1971) and in U.S. Pat. No. 3,682,777.

For the coupling of the acid IV as described above with the compound III it is also convenient and efficient to utilize as the coupling agent N-ethoxycarbonyl-2-ethoxy-1,2-dihydroquinoline (EEDQ) as described in *J. Amer. Chem. Soc.*, 90, 823–824 and 1652–1653 (1968) and U.S. Pat. No. 3,455,929. The reaction is preferably carried out at 30°–35° C. in benzene, ethanol or tetrahydrofuran using about equimolar quantities of all three reagents followed by conventional isolation.

In the treatment of bacterial infections in man, the compounds of this invention are administered parenterally, in accordance with conventional procedures for antibiotic administration, in an amount of from about 5 to 200 mg./kg./day and preferably about 5 to 20 mg./kg./day in divided dosage, e.g. three to four times a day. They are administered in dosage units containing, for example, 125, 250 or 500 mg. of active ingredient with suitable physiologically acceptable carriers or excipients. The dosage units are preferably in the form of liquid preparations such as solutions or suspensions.

Also included within the present invention are pharmaceutical compositions comprising a mixture of an antibacterially effective amount of a compound of the present invention and a semisynthetic penicillin or another cephalosporin or a cephamycin or a β-lactamase inhibitor or an aminoglycoside antibiotic.

There is further provided by the present invention a pharmaceutical composition comprising an antibacterially effective amount of a compound having the formula

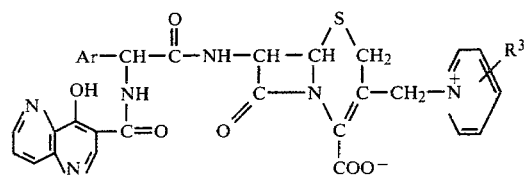

wherein Ar is

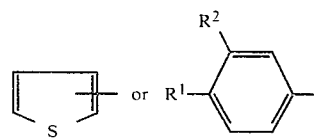

wherein $R^1$ is hydrogen or hydroxy and $R^2$ is hydrogen, hydroxy, methyl, methoxy or chloro and $R^3$ is N,N-dimethylaminomethyl and preferably $R^1$ and $R^2$ are hydrogen or $R^1$ is hydroxy and $R^2$ is hydrogen, chloro or hydroxy.

There is further provided by the present invention a method of treating bacterial infections comprising administering by injection to an infected warmblooded animal, including man, an effective by nontoxic dose of 250-1000 mgm of a compound having the formula

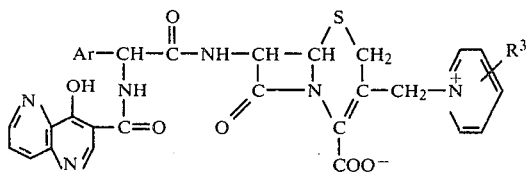

wherein Ar is

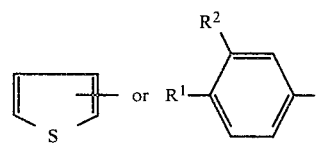

wherein $R^1$ is hydrogen or hydroxy and $R^2$ is hydrogen, hydroxy, methyl, methoxy or chloro and $R^3$ is N,N-dimethylaminomethyl and preferably $R^1$ and $R^2$ are hydrogen or $R^1$ is hydroxy and $R^2$ is hydrogen, chloro or hydroxy.

There is also provided by the present invention a method for combatting *Pseudomonas aeruginosa* infections which comprises administering to a warm-blooded mammal infected with a *Pseudomonas aeruginosa* infection an amount effective for treating said *Pseudomonas aeruginosa* infection of a composition comprising a compound having the formula

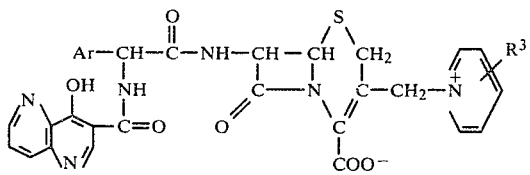

wherein Ar is

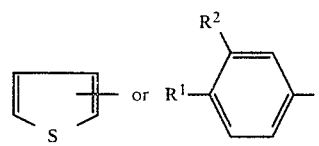

wherein $R^1$ is hydrogen or hydroxy and $R^2$ is hydrogen, hydroxy, methyl, methoxy or chloro and $R^3$ is N,N-dimethylaminomethyl and preferably $R^1$ and $R^2$ are hydrogen or $R^1$ is hydroxy and $R^2$ is hydrogen, chloro or hydroxy.

HP-20 is a macroreticular adsorbent resin in the form of insoluble beads of porous polymer. They are macroporous-nonionic, cross-linked polystyrene polymers.

The following examples are for purposes of illustration only.

DESCRIPTION OF THE PREFERRED EMBODIMENTS

EXAMPLE 1

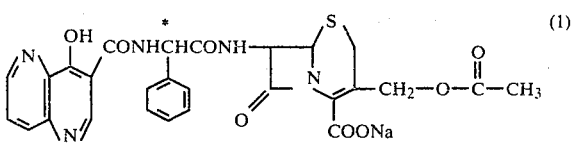

*Dextro

Sodium 7-[D-α-(4-hydroxy-1,5-naphthyridine-3-carboxamido)-α-phenylacetamido]cephalosporanate (1)

The N-hydroxysuccinimido ester of 4-hydroxy-1,5-naphthyridine-3-carboxylic acid (950 mg., 3.3 m moles) was added to a solution of the TFA (trifluoroacetic acid) salt of cephaloglycin (1.56 g., 3 m moles) and 1.3 ml. (9.3 m moles) of Et₃N in 15 ml. of DMF (dimethylformamide). The mixture was stirred overnight at room temperature and evaporated under reduced pressure. The residue was triturated with 20 ml. of dry acetone, filtered and dissolved in 4 ml. of DMF. To the solution was added 6 ml. of 1 M sodium 2-ethylhexanoate in AcOEt (ethyl acetate) solution and the mixture was stirred for 15 minutes, concentrated to a small volume under reduced pressure and diluted with 100 ml of acetone. The resulting precipitate was dissolved in 5 ml. of water and chromatographed on a column of HP-20 resin (90 ml.). The column was developed successively with water (300 ml.) and 30% aq. methanol (500 ml.) (MeOH).

The eluates were collected in 20-ml. fractions, monitoring with uv (260 mn) and tlc (silica-gel plate, CH₃CN:H₂O=4:1, detected with I₂, Rf=0.3). The fractions 15-53 were collected and concentrated to a small volume under reduced pressure. The residue was diluted with 50 ml. of acetone to separate the precipitate, which was collected by filtration and dried to afford 620 mg. (34%) of sodium 7-[D-α-(4-hydroxy-1,5-naphthyridine-3-carboxamido)-α-phenylacetamido]-cephalosporanate (1), melting at >300° C.

ir; $\nu_{max}^{KBr}$ 3450, 3300, 1765, 1650, 1610, 1530 cm⁻¹ uv; $\lambda_{max}^{pH7Buffer}$ 255 nm (ε, 35000), 295 nm (ε, 8200), 310 nm (ε, 8800), 325 nm (ε, 6500)

Anal. calcd. for C₂₇H₂₂N₅O₈SNa.3H₂O: C, 49.62; H, 4.32; N, 10.71; S, 4.91. Found: C, 49.47; H, 3.69; N, 10.86; S, 5.07.

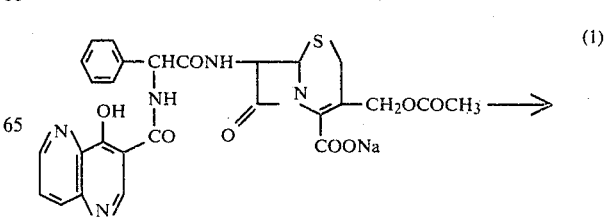

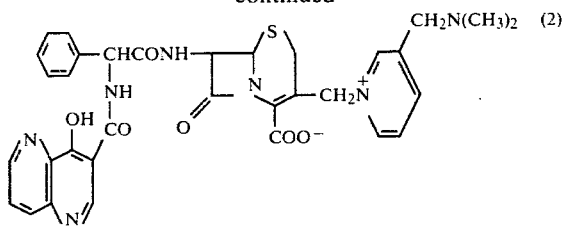

BB-S 676,
7-[D-α-(4-Hydroxy-1,5-naphthyridine-3-carboxamido)α-phenylacetamido]-3-(3-N,N-dimethylaminomethylpyridinium)methyl-3-cephem-4-carboxylate Hydrochloride (2)

A mixture of the 3-acetoxymethyl cephalosporin (1) (1.20 g.), 3-N,N-dimethylaminomethylpyridine (0.82 g.) in water (4 ml.) was adjusted at pH 7 by the addition of dil. hydrochloric acid. The solution was heated with KSCN (4.8 g.) at 60° C. overnight, then diluted with water (20 ml.) and adjusted to pH 8 with sodium bicarbonate. The dark brown precipitate was filtered, washed well with water and suspended in water (10 ml.). The mixture was acidified to pH 2 with dil. hydrochloric acid and filtered to remove insoluble materials. The filtrate was concentrated under reduced pressure and the concentrate was freeze-dried to give (2), BB-S 676 (73 mg., 5.6%), m.p. 180°-185° C. (dec.).

ir; $\nu_{max}^{KBr}$ 3600–2600, 1775, 1660, 1630, 1515 cm$^{-1}$.
uv; $\lambda_{max}^{pH7Buffer}$ 256 nm ($\epsilon$, 30000), 310 nm ($\epsilon$, 7100).
nmr; $\delta_{ppm}^{D2O}$ 2.95 (6H, s, CH$_3$), 4.55 (2H, s, pyridine-CH$_2$), 5.10 (1H, d, 4 Hz, 6-H), 5.60 (2H, s, 3—CH$_2$), 5.80 (1H, s, 4 Hz, 7—H), 7.42 (5H, m, phenyl-proton), 7.8–9.2 (8H, m, pyridine- & naphthyridine-H).

EXAMPLE 2

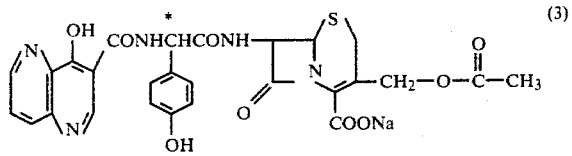

*Dextro

Sodium 7-[D-α-(4-hydroxy-1,5-naphthyridine-3-carboxamido)-α-(4-hydroxyphenyl)acetamido]cephalosporanate (3)

The N-hydroxysuccinimido ester of 4-hydroxy-1,5-naphthyridine-3-carboxylic acid (1.7 g., 6 m moles) was added to a solution of the TFA salt of 7-(D-α-amino-α-(4-hydroxyphenyl)acetamido]cephalosporanic acid (2.7 g., 5 m moles) in 20 ml. of DMF and 2.2 ml. (16 m moles) of Et$_3$N. The mixture was stirred overnight at room temperature and concentrated to a small volume under reduced pressure. The residue was triturated with 20 ml. of dry acetone, filtered and dissolved in 10 ml. of DMF. To the solution was added 10 ml. of 1 M sodium 2-ethylhexanoate in AcOEt. The mixture was stirred for 15 minutes, evaporated to a small volume and diluted with 50 ml. of acetone to separate the precipitate, which was dissolved in 15 ml. of water and chromatographed on a column of HP-20 (250 ml.). The column was developed successively with water (1 L), and 30% aq. MeOH (2 L). The eluates were collected in 20-ml. fractions monitoring with uv (260 nm) and tlc (silica-gel plate, CH$_3$CN:H$_2$O=4:1, detected with I$_2$, Rf=0.2). The fractions 52–105 were combined and concentrated to a small volume under reduced pressure. The residue was diluted with 100 ml. of dry acetone to separate the precipitate, which was collected by filtration and dried to afford 1.81 g. (59%), of sodium 7-[D-α-(4-hydroxy-1,5-naphthyridine-3-carboxamido)-α-(4-hydroxyphenyl)acetamido]cephalosporanate (3), melting at >300° C.

ir; $\nu_{max}^{KBr}$ 3450, 3210, 1765, 1650, 1610, 1530, 1520 cm$^{-1}$
uv; $\lambda_{max}^{pH7Buffer}$ 225 nm ($\epsilon$, 28000), 256 nm ($\epsilon$, 37000), 310 nm ($\epsilon$, 9600)
Anal. calcd. for C$_{27}$H$_{22}$N$_5$O$_9$SNa 3H$_2$O: C, 48.43; H, 4.21; N, 10.46; S, 4.79. Found: C, 47.93; H, 3.68; N, 10.12; S, 4.64.

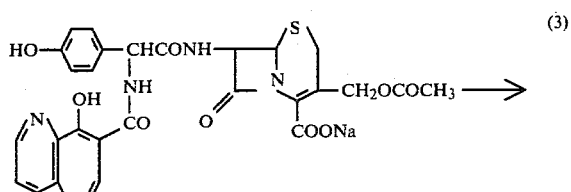

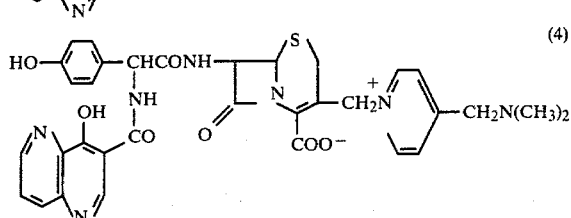

BB-S 669,
7-[D-α-(4-Hydroxy-1,5-naphthyridine-3-carboxamido)-α-(4-hydroxyphenyl)acetamido]-3-(4-N,N-dimethylaminomethylpyridinium)methyl-3-cephem-4-carboxylate Hydrochloride (4)

A solution of 4-dimethylaminomethylpyridine (816 mg., 6 m moles) in 4 ml. of water was adjusted to pH 7 with 10% HCl. To the solution were added (3) (1.2 g., 2 m moles) and KSCN (4.8 g., 49 m moles). The mixture was kept standing overnight at 57° C., diluted with 15 ml. of water and adjusted to pH 8 with NaHCO$_3$ to separate the precipitate, which was collected by filtration. The solid was washed twice with 10 ml. of water. The solid was suspended in 5 ml. of water and adjusted to pH 2.5. The mixture was filtered and the filtrate was lyophilized to give 80 mg. (5%) of (4), BB-S 669, melting at >190° C. (dec.).

ir; $\nu_{max}^{KBr}$ 3400, 3200, 1780, 1660, 1630, 1520 cm$^{-1}$
uv; $\lambda_{max}^{pH7Buffer}$ 255 nm ($\epsilon$, 29400), 310 nm ($\epsilon$, 6700).

EXAMPLE 3

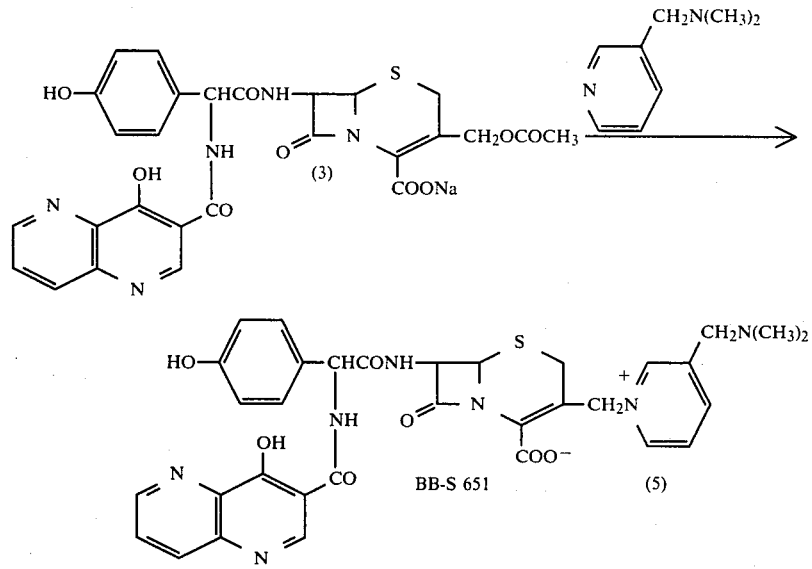

BB-S 651,
7-[D-α-(4-Hydroxy-1,5-naphthyridine-3-carboxamido)-α-(4-hydroxyphenyl)acetamido]-3-(3-N,N-dimethylaminomethylpyridinium)methyl-3-cephem-4-carboxylate Hydrochloride (5)

A solution of 3-dimethylaminomethylpyridine (3.3 g., 24 m moles) in 12 ml. of water was adjusted to pH 7 with 10% HCl. To the solution were added the cephalosporin (3) (4.8 g., 8 m moles) and KSCN (19.2 g., 0.2 mole). The mixture was stirred overnight at 54° C., diluted to about 300 ml. with water and adjusted to pH 8 with NaHCO₃. Insolubles collected by filtration were washed thoroughly with water (2×100 ml.) by agitating for 15 minutes. The insoluble solid was suspended again in 20 ml. of water and adjusted to pH 2 with 10% HCl. After filtration, the filtrate was lyophilized to afford 405 mg. (7%) of (5), BB-S 651, melting at >195° C. (dec.).

ir; $\nu_{max}^{KBr}$ 3400, 3200, 1780, 1660, 1630, 1510 cm$^{-1}$.
uv; $\lambda_{max}^{pH7Buffer}$ 255 nm (ε, 31500), 310 nm (ε, 6200).
nmr; $\delta_{ppm}^{DMSO-d_6}$ 2.80 (6H, s, N(C$\underline{H}$₃)₂), 3.55 (2H, m, 2-H), 4.60 (2H, s, C$\underline{H}$₂N), 5.13 (1H, d, J=4.5 Hz, 6-H), 5.70 (4H, m, 3-CH₂, 7-H, C$\underline{H}$-N), 6.68 & 7.25 (each 2H, d, J=9 Hz, phenyl-H), 8.0–9.5 (8H, m, aromatic-H), 10.5 (1H, d, J=7.5 Hz, disappeared by D₂O, 7-NH).

EXAMPLE 4

7-[D-α-(4-Hydroxy-1,5-naphthyridine-3-carboxamido)-α-(3,4-dihydroxyphenyl)acetamido]-3-(3-N,N-dimethylaminoethylpyridinium)methyl-3-cephem-4-carboxylate,
7-[D-α-(4-hydroxy-1,5-naphthyridine-3-carboxamido)-α-(3-chloro-4-hydroxyphenyl)acetamido]-3-(3-N,N-dimethylaminomethylpyridinium)methyl-3-cephem-4-carboxylate,
7-[D-α-(4-hydroxy-1,5-naphthyridine-3-carboxamido)-α-(3-methyl-4-hydroxyphenyl)acetamido]-3-(3-N,N-dimethylaminomethylpyridinium)methyl-3-cephem-4-carboxylate and
7-[D-α-(4-hydroxy-1,5-naphthyridine-3-carboxamido)-α-(3-methoxy-4-hydroxyphenyl)acetamido]-3-(3-N,N-dimethylaminomethylpyridinium)methyl-3-cephem-4-carboxylate respectively are prepared by substitution in the procedure of Example 1 for the
7-[D-α-amino-α-phenyl-acetamido]cephalosporanic acid (cephaloglycin) used therein of an equimolar weight of
7-[D-α-amino-α-(3,4-dihydroxyphenyl)acetamido]cephalosporanic acid,
7-[D-α-amino-α-(3-chloro-4-hydroxyphenyl)acetamido]cephalosporanic acid,
7-[D-α-amino-α-(3-methyl-4-hydroxyphenyl)acetamido]cephalosporanic acid and
7-[D-α-amino-α-(3-methoxy-4-hydroxyphenyl)acetamido]cephalosporanic acid respectively.

EXAMPLE 5

7-[D-α-(4-Hydroxy-1,5-naphthyridine-3-carboxamido)-α-(3,4-dihydroxyphenyl)acetamido]-3-(4-N,N-dimethylaminomethylpyridinium)methyl-3-cephem-4-carboxylate, 7-[D-α-(4-hydroxy-1,5-naphthyridine-3-carboxamido)-α-(3-chloro-4-hydroxyphenyl)acetamido]-3-(4-N,N-dimethylaminomethylpyridinium)methyl-3-cephem-4-carboxylate, 7-[D-α-(4-hydroxy-1,5-naphthyridine-3-carboxamido)-α-(3-methyl-4-hydroxyphenyl)acetamido]-3-(4-N,N-dimethylaminomethylpyridinium)methyl-3-cephem-4-carboxylate and 7-[D-α-(4-hydroxy-1,5-naphthyridine-3-carboxamido)-α-(3-methoxy-4-hydroxyphenyl- )acetamido]-3-(4-N,N-dimethylaminomethylpyridinium)methyl-3-cephem-4-carboxylate respectively are prepared by substitution in the procedure of Example 2 for the 7-[D-α-amino-α-(4-hydroxyphenyl)acetamido]-cephalosporanic acid used therein of an equimolar weight of 7-[D-α-amino-α-(3,4-dihydroxyphenyl)acetamido]cephalosporanic acid, 7-[D-α-amino-α-(3-chloro-4-hydroxyphenyl)acetamido]cephalosporanic acid, 7-[D-α-amino-α-(3-methyl-4-hydroxyphenyl)acetamido]cephalosporanic acid and 7-[D-α-amino-α-(3-methoxy-4-hydroxyphenyl)acetamido]cephalosporanic acid respectively.

EXAMPLE 6

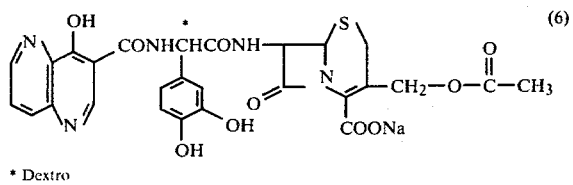

\* Dextro

Sodium 7-[D-α-(4-hydroxy-1,5-naphthyridine-3-carboxamido)-α-(3,4-dihydroxyphenyl)acetamido]cephalosporanate (6)

The N-hydroxysuccinimido ester of 4-hydroxy-1,5-naphthyridine-3-carboxylic acid (1g., 2.6 m moles) was added to a solution of the TFA salt of 7-[D-α-amino-α-(3,4-dihydroxyphenyl)acetamido]cephalosporanic acid (1 g., 1.8 m moles) Farmdoc 22850W; Japan Kokai 50-82086; U.K. 1,472,174) and 1 ml. (7.2 m moles) of Et₃N in 15 ml. of DMF. The mixture was stirred overnight at room temperature and concentrated to a small volume under reduced pressure. The concentrate was triturated with 20 ml. of dry acetone, filtered and dissolved in 5 ml. of DMF. To the solution was added sodium 2-ethylhexanoate in AcOEt (1 M solution, 6.3 ml.). The mixture was stirred for 15 minutes, concentrated to a small volume and diluted with 150 ml. of acetone to separate the precipitate, which was dissolved in 15 ml. of water and chromatographed on a column of HP-20 (90 ml.). The column was developed successively with water (1 L) and 30% aq. MeOH (1 L). The eluate was collected in 20-ml. fractions, monitoring with uv (260 nm) and tlc (silica-gel plate, CH₃CN/H₂O=4/1, detected with I₂, Rf=0.18). Fractions 51–57 were combined and concentrated in vacuo. The concentrate was diluted with 50 ml. of dry acetone to separate the precipitate, which was collected by filtration and dried to afford 310 mg. (28%) of (6), melting at >300° C.

ir; $\nu_{max}^{KBr}$ 3400, 3250, 1760, 1660, 1530 cm⁻¹.

uv; $\lambda_{max}^{pH7Buffer}$ 255 nm (ε, 16600), 275 nm (ε, 9500), 310 nm (ε, 4500).

Anal. calcd. for C₂₇H₂₂N₅O₁₀SNa.3H₂O: C, 47.30; H, 4.12; N, 10.21; S, 4.68. Found: C, 46.93; H, 4.23; N, 9.98; S, 5.94.

EXAMPLE 7

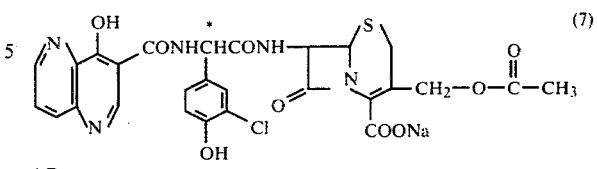

\* Dextro

Sodium 7-[D-α-(4-hydroxy-1,5-naphthyridine-3-carboxamido)-α-(3-chloro-4-hydroxyphenyl)acetamido]cephalosporanate (7)

The N-hydroxysuccinimido ester of 4-hydroxy-1,5-naphthyridine-3-carboxylic acid (565 mg, 1.97 m moles) was added to a solution of the TFA salt of 7-[D-α-amino-α-(3-chloro-4-hydroxyphenyl)acetamido]cephalosporanic acid (930 mg, 1.64 m moles) (U.S. 3,489,751) and 0.74 ml (5.3 m moles) of Et₃N in 10 ml of DMF. The mixture was stirred overnight at room temperature and concentrated to a small volume under reduced pressure. The concentrate was triturated with 30 ml of dry acetone, filtered and dissolved in 5 ml of DMF. To the solution was added 2 ml of 1 M sodium 2-ethylhexanoate in AcOEt solution. The mixture was stirred for 15 minutes, evaporated to a small volume and diluted with 50 ml of acetone to separate the precipitate (1.1 g) which was dissolved in 10 ml of water and chromatographed on a column of HP-20 (90 ml). The column was developed successively with water (400 ml) and 30% aq. MeOH (1 L). The eluate was collected in 20-ml fractions monitoring with tlc (silica gel plate, CH₃CN/H₂O=4/1, detected with I₂, Rf=0.2). Fractions 22–37 were combined and concentrated to a small volume in vacuo. The residue was diluted with 50 ml of dry acetone to separate the precipitate, which was collected by filtration and dried to afford 620 mg (58%) of the desired compound 7, melting at >300° C.

ir; $\nu_{max}^{KBr}$ 3400, 3250, 1765, 1650, 1610, 1570, 1530 cm⁻¹.

uv; $\lambda_{max}^{1\%NaHCO_3}$ 262 nm (ε, 44000), 310 nm (ε, 10000).

Anal. calcd. for C₂₇H₂₁N₅O₉ClSNa.4H₂O: C, 44.91; H, 4.05; N, 9.70; S, 4.44. Found: C, 44.80; H, 3.39; N, 9.68; S, 4.42.

EXAMPLE 8

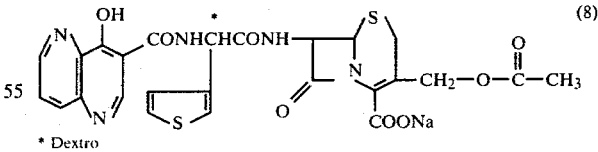

\* Dextro

Sodium 7-[D-α-(4-hydroxy-1,5-naphthyridine-3-carboxamido)-α-(3-thienyl)acetamido]cephalosporanate (8)

The N-hydroxysuccinimido ester of 4-hydroxy-1,5-naphthyridine-3-carboxylic acid (714 mg, 2.5 m moles) was added to a solution of the TFA salt of 7-[D-α-amino-α-(3-thienyl)acetamido]cephalosporanic acid (1.09 g, 2.07 m moles) and 0.93 ml (6.6 m moles) of Et₃N in 10 ml of DMF. The mixture was stirred overnight at room temperature and concentrated to a small volume under reduced pressure. The residue was triturated with 30 ml of acetone, filtered and dissolved in 5 ml of DMF. To the solution was added 2 ml of 1 M sodium 2-ethylhexanoate in AcOEt solution. The mixture was evaporated to a small volume and diluted with 50 ml of acetone to separate the precipitate (1.3 g) which was dissolved in 10 ml of water and chromatographed on a column of HP-20 (90 ml). The column was developed successively with water (800 ml) and 30% aq. MeOH (1 L). The eluate was collected in 20-ml fractions monitoring with tlc (silica gel, $CH_3CN/H_2O=4/1$, detected with $I_2$, Rf=0.4). Fractions 43–59 were combined and concentrated to a small volume in vacuo. The residue was diluted with 100 ml of dry acetone to separate the precipitate, which was collected by filtration and dried to afford 680 mg (54%) of the desired compound (8), melting at >300° C.

ir; $\nu_{max}^{KBr}$ 3400, 3250, 1765, 1650, 1610, 1570, 1530 cm$^{-1}$.

uv; $\lambda_{max}^{pH7Buffer}$ 255 nm ($\epsilon$, 36000), 310 nm ($\epsilon$, 9100).

Anal. calcd. for $C_{25}H_{20}N_5O_8S_2Na.2H_2O$: C, 46.80; H, 3.77; N, 10.92; S, 9.99. Found: C, 46.24; H, 3.33; N, 10.86; S, 9.54.

EXAMPLE 9

Sodium 7-[D-α-4-hydroxy-1,5-naphthyridine-3-carboxamido)-α-(3-methyl-4-hydroxyphenyl)acetamido]cephalosporanate The title compound is prepared by substituting in the procedure of Example 6 for the TFA (trifluoroacetic acid) salt of 7-[D-α-amino-α-(3,4-dihydroxyphenyl)acetamido]cephalosporanic acid used therein of an equimolar weight of the TFA salt of 7-[D-α-amino-α-(3-methyl-4-hydroxyphenyl)acetamido]cephalosporanic acid.

EXAMPLE 10

Sodium 7-[D-α-4-hydroxy-1,5-naphthyridine-3-carboxamido)-α-(3-methoxy-4-hydroxyphenyl)acetamido]cephalosporanate The title compound is prepared by substituting in the procedure of Example 6 for the TFA (trifluoroacetic acid) salt of 7-[D-α-amino-α-(3,4-dihydroxyphenyl)acetamido]cephalosporanic acid used therein of an equimolar weight of the TFA salt of 7-[D-α-amino-α-(3-methoxy-4-hydroxyphenyl)acetamido]cephalosporanic acid.

Illustrative Results of Biological Testing

In vitro activity of BB-S 651 and BB-S 669 and BB-S 676

Minimum inhibitory concentrations (MIC) of BB-S 651, BB-S 669 and BB-S 676 were determined by serial two-fold agar dilution method using Steers' apparatus on Mueller-Hinton agar plate against 15 test organisms for primary screening as shown in Table 1. Table 2 shows the results of more extensive testing of BB-S 651.

TABLE 1

In vitro activity of the 3-pyridiniummethyl cephalosporins (Mueller-Hinton agar)

| Organisms | | MIC (mcg/ml) | | | |
|---|---|---|---|---|---|
| | | BB-S651 | BB-S669 | BB-S676 | Carbenicillin |
| S. aureus Smith | A9537 | 3.1 | 6.3 | 3.1 | 0.2 |
| S. aureus 209P | A9497 | 0.8 | 3.1 | 1.6 | 0.2 |
| S. aureus #193[1] | | 6.3 | 25 | 6.3 | 12.5 |
| S. aureus BX-1633-2 | A9606[1] | 6.3 | 25 | 6.3 | 12.5 |
| E. coli Juhl | A15119[2] | 6.3 | 1.6 | 12.5 | 3.1 |
| E. coli | A9660[2] | 1.6 | 0.8 | 3.1 | 0.8 |
| E. coli | A15148[3] | 3.1 | 0.8 | 6.3 | 3.1 |
| E. coli | A15164[3] | 25 | 6.3 | 50 | 6.3 |
| E. cloacae | A9656 | 12.5 | 3.1 | 50 | 3.1 |
| S. marcescens | A20019 | 50 | 12.5 | 50 | 3.1 |
| Ps. aeruginosa | A15150 | 0.8 | 0.8 | 1.6 | 25 |
| Ps. aeruginosa | A9843 | 1.6 | 1.6 | 3.1 | 50 |
| Ps. aeruginosa | A20717 | 1.6 | 3.1 | 6.3 | >100 |
| Ps. aeruginosa | A20718 | 0.8 | 0.8 | 1.6 | 25 |
| Ps. aeruginosa | A20229 | 0.8 | 1.6 | 3.1 | 50 |

[1]Penicillinase-producing strains
[2]Cephalothin-sensitive strains
[3]Cephalothin-resistant strains

TABLE 2

In vitro activity of BB-S 651

| | No. of strain | Geometric mean of MIC (mcg/ml) | |
|---|---|---|---|
| | | BB-S 651 | Cefoperazone (T-1551) |
| Gp-Ia | | | |
| S. aureus | 12 | 3.7 | 1.6 |
| Gp-Ib | | | |
| S. aureus | 16 | 42 | 17 |
| Gp-II | | | |
| S. pyogenes | 10 | 0.4 | 0.2 |
| S. pneumoniae | 9 | 0.8 | 0.8 |
| Gn-Ia | | | |
| E. coli | 7 | 2.6 | 0.2 |
| K. pneumoniae | 10 | 18 | 0.9 |
| P. mirabilis | 6 | >100 | 0.8 |
| Gn-Ib | | | |
| E. coli | 13 | 29 | 3.7 |
| K. pneumoniae | 5 | >100 | 100 |
| P. mirabilis | 2 | >100 | 12.5 |
| Gn-II | | | |
| E. cloacae | 7 | >100 | 28 |
| S. marcescens | 10 | >100 | 47 |
| Indole(+) Proteus sp. | 8 | >100 | 3.5 |
| P. stuartii | 5 | 1.6 | 0.8 |
| Gn-III | | | |
| P. aeruginosa | 32 | 1.7 | 11 |
| P. maltophilia | 13 | 14 | 47 |
| P. putida | 5 | 22 | >100 |
| P. cepacia | 4 | 59 | >100 |
| P. melanogenum | | | |
| Gn-IV | | | |
| H. influenzae | 4 | 0.8 | 0.8 |
| Neisseria sp. | 6 | 1.6 | 0.8 |

In vivo activity of BB-S 651

The in vivo efficacy of BB-S 651 was evaluated by intramuscular treatment against experimental infection in mice. The activity was compared with cefoperazone (T-1551). Mice were challenged intraperitoneally with approximately a 100×LD$_{50}$ dose of the pathogens in a 5% mucin suspension. The mice were treated with test compound by im route immediately after the bacterial challenge. A group of five mice were used for each dosage level and the animals were observed for 5 days to determine the median protective dose (PD$_{50}$). The results are summarized in Table 5.

Antibiotic blood levels were determined in mice following intramuscular administration of the test compounds at 20 mg/kg. The blood samples were collected from the orbital sinuses into heparinized capillary tubes at 15, 30, 60 and 120 minutes after administration. The antibiotic concentration was determined by the paper disc-agar diffusion method using *E. coli* NIHJ or *S. lutea* PCI 1001 as the assay organism. The results are shown in Tables 3 and 4.

TABLE 3

Mouse blood levels of BB-S 651

| Dose | Time | Mouse, i.m. Blood level (mcg/ml) | |
|---|---|---|---|
| | | BB-S 651 | T-1551 (cefoperazone) |
| 40 mg/kg | 15' | 25 | 19 |
| | 30' | 18 | 14 |
| | 60' | 11 | 2.5 |
| | 120' | 3 | <0.4 |
| 20 mg/kg | 15' | 11 | 9 |
| | 30' | 9 | 5.5 |
| | 60' | 5 | 1.3 |
| | 120' | <0.4 | <0.4 |
| 10 mg/kg | 15' | 5 | 3.5 |
| | 30' | 3 | 1.8 |
| | 60' | <0.4 | <0.4 |
| | 120' | <0.4 | <0.4 |

TABLE 4

Additional Mouse blood levels of BB-S 651

| Dose | Time (hour) | Blood level (mice, im), mcg/ml | |
|---|---|---|---|
| | | BB-S 651 | cefoperazone |
| 40 mg/kg | ¼ | 20 | 18 |
| | ½ | 14 | 12 |
| | 1 | 10 | 5.4 |
| | 2 | 3 | 1.2 |
| 20 | ¼ | 10 | 10.5 |
| | ½ | 7.4 | 6.3 |
| | 1 | 5.8 | 2.5 |
| | 2 | <0.8 | <0.8 |
| 10 | ¼ | 4.3 | 5 |
| | ½ | 3.3 | 3.5 |
| | 1 | 2.5 | 1.2 |
| | 2 | <0.8 | <0.8 |

TABLE 5

In vivo activity of BB-S 651

| Test Organism | PD50 (mice, im), mg/kg | |
|---|---|---|
| | BB-S 651 | cefoperazone |
| *S. aureus* Smith A9537 | 1.1 | 2.4 |
| *S. aureus* BX-1633 A9606 | 6.3 | 1.6 |
| *S. pyogenes* A20201 | 1.1 | 2.5 |
| *E. coli* Juhl A15119 | 1.9 | 1.1 |
| *K. pneumoniae* A9977 | 7.4 | 0.6 |
| *P. morganii* A15153 | >100 | 6.3 |
| *P. mirabilis* A9900 | >25 | 6.3 |
| *P. aeruginosa* A9843 | 1.9 | 20 |
| *P. aeruginosa* A21509 | 3.2 | 30 |

Starting Materials

The preparation and properties of 2-, 3- and 4-N,N-dimethylaminomethylpyridines were described by Barlow et al., Brit. J. Pharmacol., 18, 510–542 (1962).

This invention is capable of industrial application.

We claim:

1. A compound having the D-configuration in the 7-sidechain and the formula

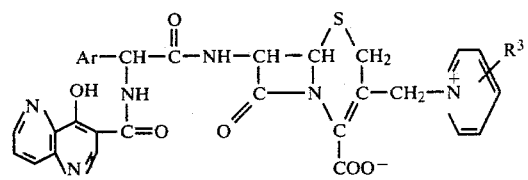

wherein Ar is

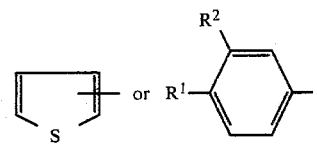

wherein $R^1$ is hydrogen or hydroxy and $R^2$ is hydrogen, hydroxy, methyl, methoxy or chloro and $R^3$ is N,N-dimethylaminomethyl.

2. A compound having the D-configuration in the 7-sidechain and the formula

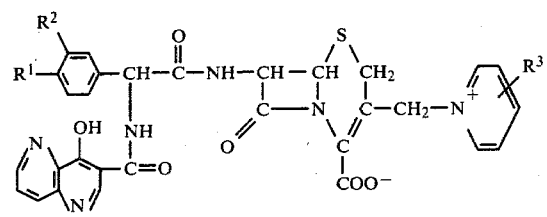

wherein $R^1$ is hydrogen or hydroxy and $R^2$ is hydrogen, hydroxy, methyl, methoxy or chloro and $R^3$ is N,N-dimethylaminomethyl.

3. A compound having the D-configuration in the 7-sidechain and the formula

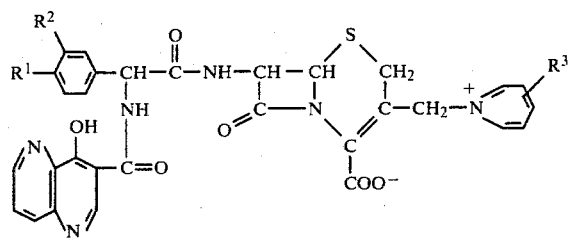

wherein $R^1$ is hydrogen or hydroxy and $R^2$ is hydrogen and $R^3$ is N,N-dimethylaminomethyl.

4. A compound having the D-configuration in the 7-sidechain and the formula

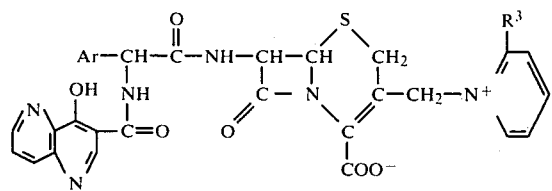

wherein Ar is

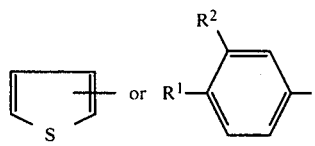

wherein R¹ is hydrogen or hydroxy and R² is hydrogen, hydroxy, methyl, methoxy or chloro and R³ is N,N-dimethylaminomethyl.

5. A compound having the D-configuration in the 7-sidechain and the formula

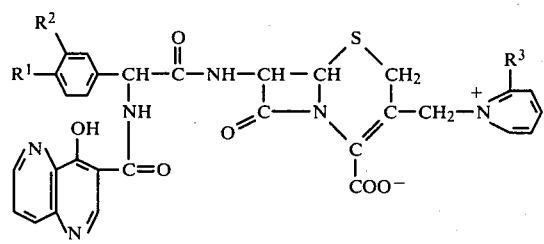

wherein R¹ is hydrogen or hydroxy and R² is hydrogen, hydroxy, methyl, methoxy or chloro and R³ is N,N-dimethylaminomethyl.

6. A compound having the D-configuration in the 7-sidechain and the formula

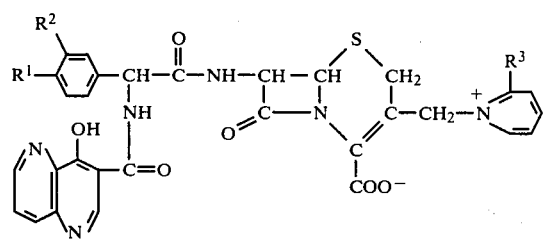

wherein R¹ is hydrogen or hydroxy and R² is hydrogen and R³ is N,N-dimethylaminomethyl.

7. A compound having the D-configuration in the 7-sidechain and the formula

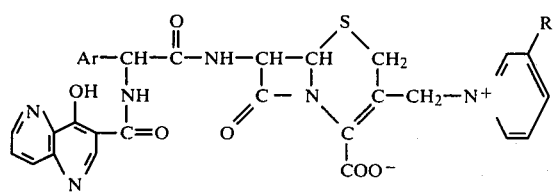

wherein Ar is

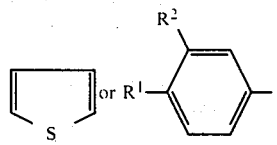

wherein R¹ is hydrogen or hydroxy and R² is hydrogen, hydroxy, methyl, methoxy or chloro and R³ is N,N-dimethylaminomethyl.

8. A compound having the D-configuration in the 7-sidechain and the formula

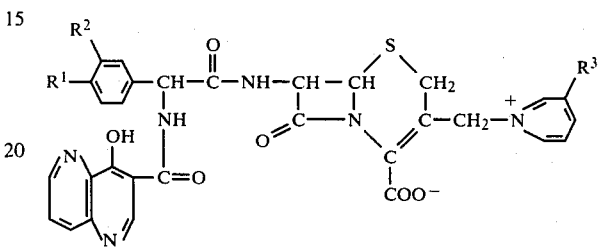

wherein R¹ is hydrogen or hydroxy and R² is hydrogen, hydroxy, methyl, methoxy or chloro and R³ is N,N-dimethylaminomethyl.

9. A compound having the D-configuration in the 7-sidechain and the formula

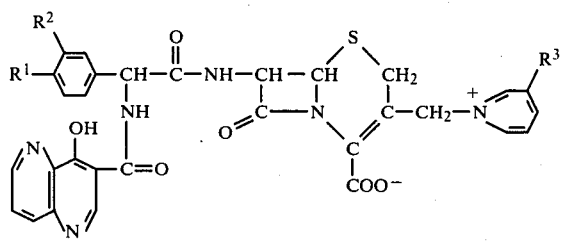

wherein R¹ is hydrogen or hydroxy and R² is hydrogen and R³ is N,N-dimethylaminomethyl.

10. A compound having the D-configuration in the 7-sidechain and the formula

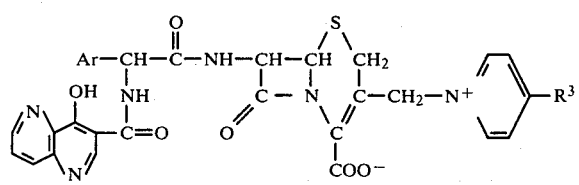

wherein Ar is

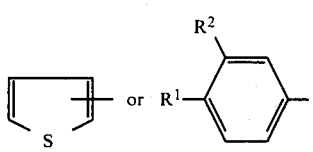

wherein R¹ is hydrogen or hydroxy and R² is hydrogen, hydroxy, methyl, methoxy or chloro and R³ is N,N-dimethylaminomethyl.

11. A compound having the D-configuration in the 7-sidechain and the formula

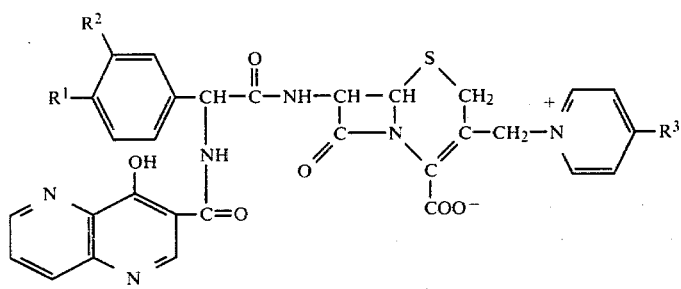

wherein R¹ is hydrogen or hydroxy and R² is hydrogen, hydroxy, methyl, methoxy or chloro and R³ is N,N-dimethylaminomethyl.

12. A compound having the D-configuration in the 7-sidechain and the formula

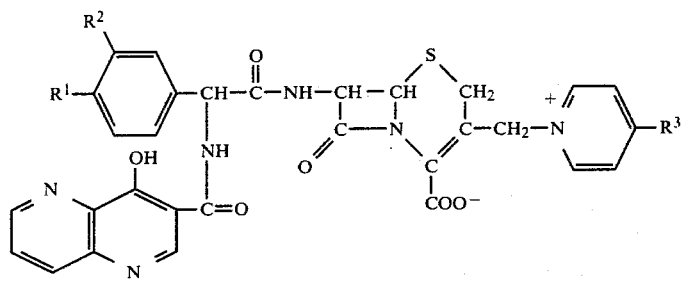

wherein R¹ is hydrogen or hydroxy and R² is hydrogen and R³ is N,N-dimethylaminomethyl.

13. 7-[D-α-(4-Hydroxy-1,5-naphthyridine-3-carboxamido)-α-phenylacetamido]-3-(3-N,N-dimethylaminomethylpyridinium)methyl-3-cephem-4-carboxylate.

14. 7-[D-α-(4-Hydroxy-1,5-naphthyridine-3-carboxamido)-α-phenylacetamido]-3-(4-N,N-dimethylaminomethylpyridinium)methyl-3-cephem-4-carboxylate.

15. 7-[D-α-(4-Hydroxy-1,5-naphthyridine-3-carboxamido)-α-(4-hydroxyphenyl)acetamido]-3-(3-N,N-dimethylaminomethylpyridinium)methyl-3-cephem-4-carboxylate.

16. 7-[D-α-(4-Hydroxy-1,5-naphthyridine-3-carboxamido)-α-(4-hydroxyphenyl)acetamido]-3-(4-N,N-dimethylaminomethylpyridinium)methyl-3-cephem-4-carboxylate.

17. 7-[D-α-(4-Hydroxy-1,5-naphthyridine-3-carboxamido)-α-(3,4-dihydroxyphenyl)acetamido]-3-(3-N,N-dimethylaminomethylpyridinium)methyl-3-cephem-4-carboxylate.

18. 7-[D-α-(4-Hydroxy-1,5-naphthyridine-3-carboxamido)-α-(3,4-dihydroxyphenyl)acetamido]-3-(4-N,N-dimethylaminomethylpyridinium)methyl-3-cephem-4-carboxylate.

19. 7-[D-α-(4-Hydroxy-1,5-naphthyridine-3-carboxamido)-α-(3-chloro-4-hydroxyphenyl)acetamido]-3-(3-N,N-dimethylaminomethylpyridinium)methyl-3-cephem-4-carboxylate.

20. 7-[D-α-(4-Hydroxy-1,5-naphthyridine-3-carboxamido)-α-(3-chloro-4-hydroxyphenyl)acetamido]-3-(4-N,N-dimethylaminomethylpyridinium)methyl-3-cephem-4-carboxylate.

21. 7-[D-α-(4-Hydroxy-1,5-naphthyridine-3-carboxamido)-α-(3-methyl-4-hydroxyphenyl)acetamido]-3-(3-N,N-dimethylaminomethylpyridinium)methyl-3-cephem-4-carboxylate.

22. 7-[D-α-(4-Hydroxy-1,5-naphthyridine-3-carboxamido)-α-(3-methyl-4-hydroxyphenyl)acetamido]-3-(4-N,N-dimethylaminomethylpyridinium)methyl-3-cephem-4-carboxylate.

23. 7-[D-α-(4-Hydroxy-1,5-naphthyridine-3-carboxamido)-α-(3-methoxy-4-hydroxyphenyl)acetamido]-3-(3-N,N-dimethylaminomethylpyridinium)methyl-3-cephem-4-carboxylate.

24. 7-[D-α-(4-Hydroxy-1,5-naphthyridine-3-carboxamdio)-α-(3-methoxy-4-hydroxyphenyl)acetamido]-3-(4-N,N-dimethylaminomethylpyridinium)methyl-3-cephem-4-carboxylate.

25. 7-[D-α-(4-Hydroxy-1,5-naphthyridine-3-carboxamido)-α-(3-thienyl)acetamido]-3-(3-N,N-dimethylaminomethylpyridinium)methyl-3-cephem-4-carboxylate.

26. 7-[D-α-(4-Hydroxy-1,5-naphthyridine-3-carboxamido)-α-(3-thienyl)acetamido]-3-(4-N,N-dimethylaminomethylpyridinium)methyl-3-cephem-4-carboxylate.

* * * * *